United States Patent
Haberer et al.

(10) Patent No.: US 6,859,741 B2
(45) Date of Patent: Feb. 22, 2005

(54) DEVICE AND METHOD FOR ADAPTING THE SIZE OF AN ION BEAM SPOT IN THE DOMAIN OF TUMOR IRRADIATION

(75) Inventors: Thomas Haberer, Darmstadt (DE); Wolfgang Ott, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 7 days.

(21) Appl. No.: 10/399,888
(22) PCT Filed: Nov. 21, 2001
(86) PCT No.: PCT/EP01/13571
§ 371 (c)(1), (2), (4) Date: Jul. 11, 2003
(87) PCT Pub. No.: WO02/41948
PCT Pub. Date: May 30, 2002

(65) Prior Publication Data
US 2004/0104354 A1 Jun. 3, 2004

(30) Foreign Application Priority Data
Nov. 21, 2000 (DE) .......................................... 100 57 824

(51) Int. Cl.[7] .......................... G01B 5/28; G01N 23/00; H01J 37/317
(52) U.S. Cl. ................... 702/40; 250/491.1; 250/492.2; 250/492.3; 702/155
(58) Field of Search ............................. 702/40, 81, 95, 702/155, 157, 172; 250/491.1, 492.2, 492.3

(56) References Cited

U.S. PATENT DOCUMENTS

| | | | | | |
|---|---|---|---|---|---|
| 5,132,544 | A | * | 7/1992 | Glavish | 250/492.2 |
| 6,476,403 | B1 | * | 11/2002 | Dolinskii et al. | 250/492.3 |
| 6,677,597 | B1 | * | 1/2004 | Haberer et al. | 250/491.1 |

FOREIGN PATENT DOCUMENTS

| | | |
|---|---|---|
| DE | 198 35 209 A | 2/2000 |
| EP | 0 986 070 A | 3/2000 |
| EP | 1 041 579 A | 10/2000 |
| EP | 1 045 399 A | 10/2000 |

* cited by examiner

Primary Examiner—John Barlow
Assistant Examiner—John Le
(74) Attorney, Agent, or Firm—Frommer Lawrence & Haug LLP; Ronald R. Santucci (57) ABSTRACT

The invention relates to an apparatus and to a method for adapting the size of an ion beam spot in tumor irradiation. For that purpose, the apparatus has a raster scanning device composed of raster scanning magnets (20) for raster scanning the ion beam (19). In addition, the apparatus comprises quadrupole magnets (10) determining the size of the ion beam spot, which quadrupole magnets (10) are arranged directly in front of the raster scanning magnets (20), and finally two magnet power supply units (18) for the quadrupole doublet of the quadrupole magnets (10) determining the size of the ion beam spot, the apparatus having a control loop for obtaining current correction values, by comparing desired and actual values of the prevailing dimension of the beam, for two magnet power supply units (18) of the quadrupole doublet arranged directly in front of the raster scanning magnets (20), for defined homogenization and/or for defined variation of the size of the ion beam spot.

17 Claims, 5 Drawing Sheets

DEVICE AND METHOD FOR ADAPTING THE SIZE OF AN ION BEAM SPOT IN THE DOMAIN OF TUMOR IRRADIATION

This application is 371 of PCT/EP01/13571 filed on Nov. 21, 2001, pushed on May 30, 2002 under publication number WO 02/41948 A1 which claims priority benefits from German patent application number DE 100 57 824.1 filed Nov. 21, 2000.

The invention relates to an apparatus for adapting the size of an ion beam spot in tumour irradiation according to the precharacterising clause of claim 1 and to a method for adapting the size of an ion beam spot according to the independent method claim.

An apparatus corresponding to the precharacterising clause of claim 1 and an intensity-controlled raster scanning process are known from the article by Th. Haberer, W. Becher, D. Schardt and G. Kraft "Magnetic scanning system for heavy ion therapy" published in Nuclear Instruments and Methods in Physics Research, A330 (1993), pages 206–305. There are further known from Patent Application DE 198 35 209.3, "Apparatus and method for controlling an irradiation device", an apparatus and a method based on a control system that renders possible reliable scanning of a tumour volume of a patient by means of a raster scanning process. That apparatus has the disadvantage, however, that it is not possible without a great deal of effort to adjust the size of the ion beam spot during and between the irradiation points and therefore the size of the ion beam spot remains the same width during every section through the tumour volume and thus, in particular, does not permit sharp outlines in the edge region.

The object of further developing that control system is to obtain an increase in the geometrical precision of the dose application and a marked enhancement of the robustness of the process towards beam position variations, especially also in view of the future use of rotatable beam guides (gantries) with integrated raster scanning technology.

The magnitude of the unavoidable beam position variations which are caused by more difficult ion-optical conditions increases in the case of rotatable beam guides (gantries). Even if the intensity of the therapy beam varies between maximum value and minimum value by a factor of 30, the beam position variation of the therapy beam supplied by the accelerator should and must be within a range of ±2 mm. It is accordingly also an object of the invention to implement a precise irradiation plan so that the dose distribution resulting from the total irradiation deviates from the planned dose distribution by on average less than 5%.

That object is achieved with the subject-matter of the independent claims. Features of advantageous developments of the invention will be apparent from the dependent claims.

According to the invention, the apparatus for adapting the size of an ion beam spot in tumour irradiation has a raster scanning device composed of raster scanning magnets for raster scanning the ion beam. In addition, quadrupole magnets which determine the size of the ion beam spot are provided directly in front of the raster scanning magnets. The quadrupole doublet of the quadrupole magnets determining the size of the beam spot is powered according to the invention by two magnet power supply units.

In an apparatus used hitherto, during extraction of the therapy beam from a suitable accelerator, such as a synchrotron, variations with time of ion-optical parameters in the accelerator or of the subsequent beam guide can give rise to both beam position variations and variations with time of the beam spot sizes. While the partial problem of beam position variations has meanwhile been solved extremely effectively, there has not hitherto been any method for reducing or controlling variations in the size of the beam spot.

The aim of tumour ion-irradiation, however, is to produce particle allocations that are as exact as possible, that is to say, within the target volume the deviations from the planned dose distribution are to be minimised, the beam width variations are tolerable only to a limited extent since otherwise the geometrical pattern of the beam positions, which has been previously specified when planning the irradiation, is able to provide sufficiently exact irradiation results only for a defined range of the beam width.

For that reason, according to the invention the apparatus has a control loop that provides current correction values, by comparing desired and actual values of the prevailing beam count, for two magnet power supply units of the quadrupole doublet arranged directly in front of the raster scanning magnets and provides a defined homogenization and/or a defined variation of the size of the beam spot during beam extraction and/or from measuring cycle to measuring cycle and/or from beam position to beam position.

Figure 2:
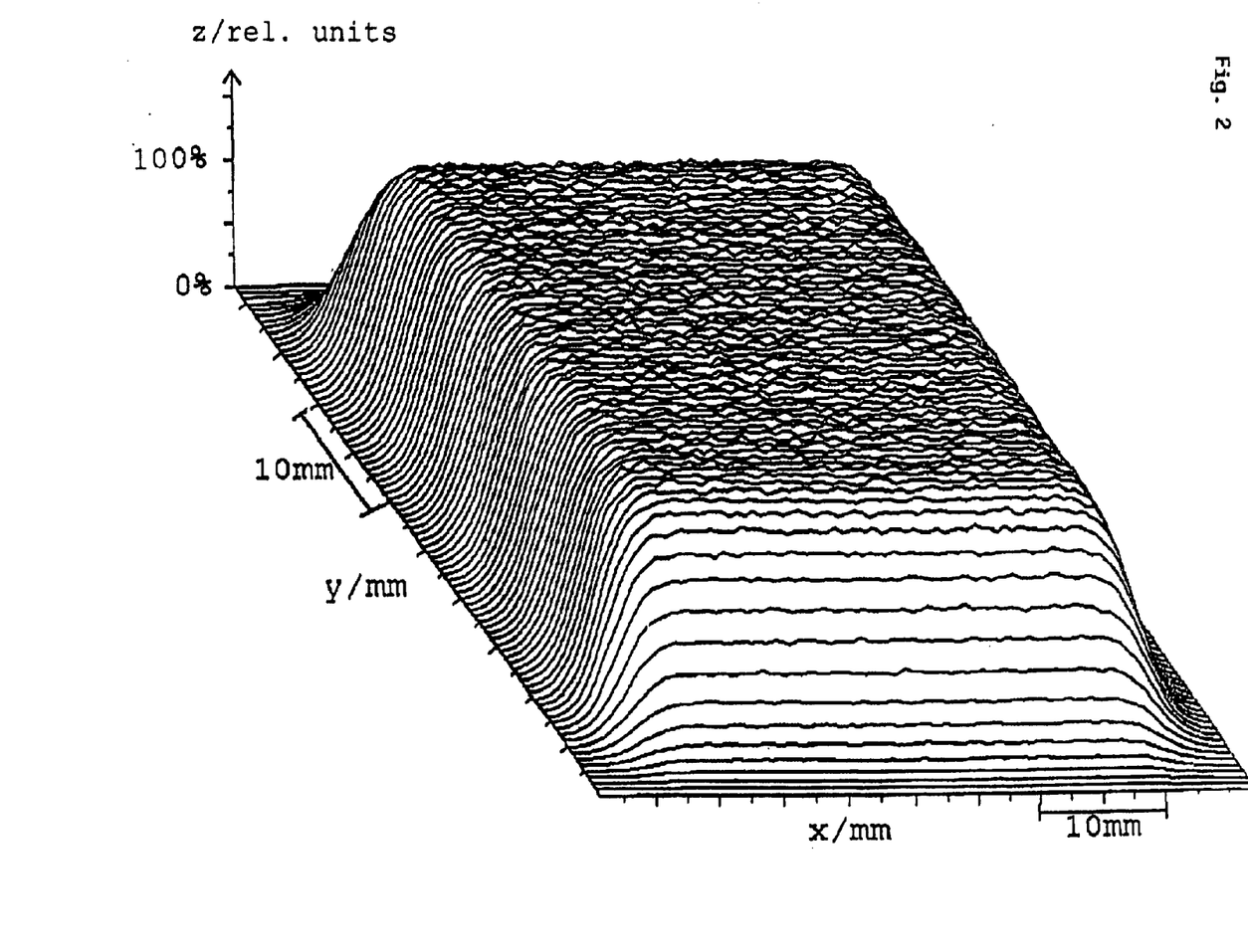
FIG. 2 shows an example of a homogeneous dose distribution with an adequate beam full width at half maximum.

The solution according to the invention has the advantage that a sensible ratio of beam profile width to beam position spacing can be maintained during the irradiation, thereby providing homogeneous dose distributions that meet the medical requirements, as shown in FIG. 2.

In order to obtain such a homogeneous beam distribution, the apparatus preferably has real-time software for calculating the actual values of the ion beam width from raw detector data. In addition, the apparatus has a position-sensitive detector for detecting the ion beam width and for producing raw detector data on the ion beam width. An advantage of that embodiment of the invention is that it enables very steep dose gradients to be produced at the edge of the volume being irradiated by varying the width of the ion beam towards the edge.

Figure 3:
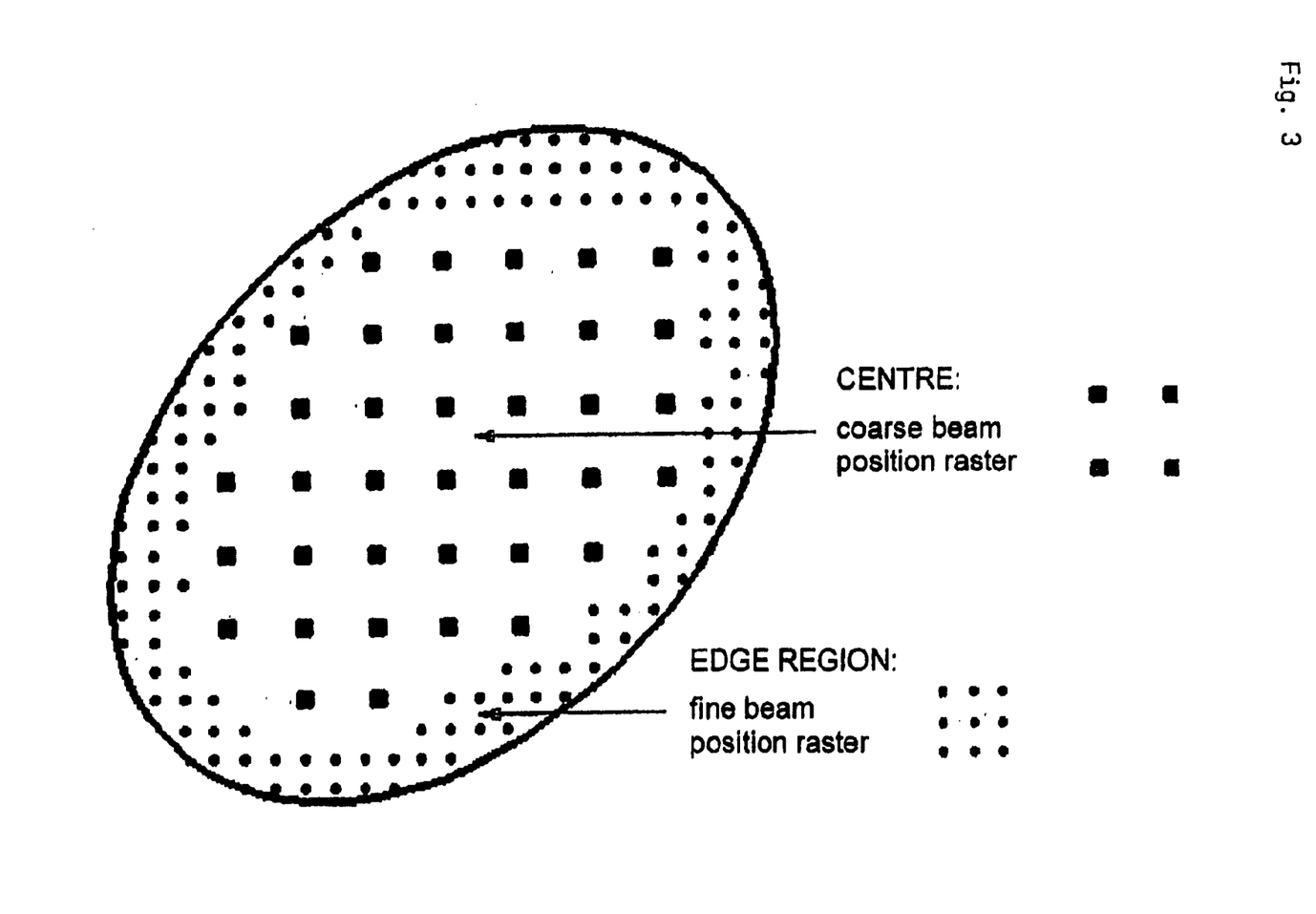
FIG. 3 shows an illustrative embodiment of a beam position distribution that becomes possible by employing the apparatus according to the invention.

The size of the beam spot is minimised towards the edge for a steep edge drop, so that the range of that drop in dose scaled with the full width at half maximum of the therapy beam is possible. The advantage associated with that apparatus for regulating the size of the beam spot is that the duration of irradiation for the patient in the irradiation chamber, with the patient in an immobilised position, can be minimised since a large ion beam spot size can be implemented in wide regions of the tumour volume and it is only towards the edge that the size of the ion beam spot is reduced and the beam positions are made denser per unit of area, as shown in FIG. 3, in order to achieve a more precise tracing of the edge.

The duration of an irradiation and hence also the patient throughput of a system is reduced by the reduced density of the beam positions in the volume of the tumour since, as the density of the beam positions decreases, the duration of the irradiation also decreases. Thus, a reduction in the duration of the irradiation is advantageously obtained as a result of the possibility of adjusting the size of the beam spot, since fewer beam positions at a greater spacing can be planned in the inner volume of the tumour. In order, on the other hand, to ensure an adequate quality of the particle allocations over the cross-section of the tumour, however, a minimum width of beam spot is required for a given beam position spacing. That in turn is ensured by the apparatus according to the invention.

In a further preferred embodiment of the apparatus, it has control and read-out modules and associated data connections in order to send information on the actual value of ion beam widths to a storage, control and read-out module and store the measurement data. That embodiment of the invention has the advantage that, by interaction of the control and read-out module with the magnet power supply units of the quadrupole doublet of the quadrupole magnets determining the size of the ion beam spot, speedy variation of the size of the ion beam spot can be ensured.

In a further embodiment of the invention, the read-out module has a number of free interfaces and a computing capacity by means of which the tracking of the ion beam width can be performed. The requirement of a steep and precise edge drop with minimum duration of the irradiation, which is understandable from a medicotechnological viewpoint, is therefore advantageously achieved with regard to the size of the irradiation spot, which cannot be achieved in the current state of the art because of the rigid size of the ion beam spot. With the ability to track and to adjust the size of the beam spot and the position of the beam spot dynamic adaptation during the irradiation of a tumour volume is advantageously obtained, whereby the person planning the irradiation is also provided with greater flexibility in specifying the beam position pattern, and the quality of the dose distribution can be further enhanced.

In an alternative embodiment of the apparatus, a control system that is expanded by one control and read-out module is provided, the additional control and read-out module being able to perform exclusively the function of ion beam width regulation. With that embodiment, rapid adjustment becomes possible in periods of time that are substantially shorter than typical accelerator cycle times.

In a further preferred embodiment of the invention, the apparatus has a control loop which starts from a multiwire ionization chamber with attached control and read-out module and leads to a control and read-out module that provides measurement data for graphical representation and actuates two magnet power supply units for horizontal and vertical focusing of the quadrupole doublet directly in front of the raster scanning magnet. Corrected field settings are thereby advantageously produced, which improve the focusing state of the system. The control is able to ensure in an advantageous manner both the maintenance of a constant size of ion beam spot during the scanning process and the defined variation of the size of the ion beam spot in accordance with an irradiation planning procedure. In that control process, the information on the variation of the beam width with time which is available from the position measurement of the raster scanning system is combined with the ability of the control system to apply to the magnet power supply units of magnets that influence the size of the ion beam spot, such as, for example, quadrupole magnets, new desired values in rapid succession, so that, from a current comparison of desired and actual value of the prevailing dimension of the beam, it is possible to calculate current correction values for both magnet power supply units of a quadrupole doublet directly in front of the raster scanning magnet.

A method for adapting the size of an ion beam spot in tumour treatment is characterised by the following method steps:

dynamic adaptation of the size of an ion beam spot in real time by applying desired values for different ion beam spot sizes to the quadrupole magnet determining the size of the ion beam spot within an acceleration cycle and/or between two successive acceleration cycles and/or between adjacent beam positions by means of adjustable frequency, obtaining current correction values, by comparing desired and actual values of the prevailing dimension of the beam, for two magnet power supply units of the quadrupole doublet of the quadrupole magnets determining the size of the ion beam spot, for defined homogenization and/or for defined variation of the size of the ion beam spot during beam extraction and/or from measuring cycle to measuring cycle and/or from beam position to beam position, irradiating tumour tissue with a denser ion beam position raster and, at the same time, a smaller ion beam spot size in the edge region than in the volume region of the tumour.

The method according to the invention thus improves the previously described raster scanning process in several respects. Owing to the possibility of setting the size of the ion beam spot in real time, the quality of the particle allocations produced by the raster scanner can be enhanced by actively adapting the current beam width to the specifications of the irradiation plan by means of a control process. The geometrical density of the beam positions can thereby be reduced in comparison with the previous irradiation mode, especially since previously it was necessary to have a reserve in order to compensate for the variations in beam width which always occurred. The control process according to the invention, which minimises those variations, provides the possibility of planning a smaller number of beam positions, which leads to shorter irradiation times and a higher patient throughput.

In a preferred implementation example of the method, the beam full width at half maximum is adapted to the ion beam position raster in such a way that, in the case of the fine ion beam position raster in the edge region, a smaller beam full width at half maximum is set than in the volume region of the tumour with a coarse ion beam position pattern. As a result, it is advantageously possible to obtain a more precise demarcation between tumour tissue and healthy tissue in the edge region since, at the same time, the beam full width at half maximum is set smaller and therefore in a more sharply defined manner than in the volume region of the tumour. By means of the greater beam full width at half maximum in the volume region of the tumour with a coarse ion beam pattern, the total number of beam positions per isoenergy section, that is to say per irradiation plane, can advantageously be reduced and therefore the irradiation treatment time can be reduced. On the other hand, the dose gradient at the edge of the tumour tissue is very steep and thus ensures precise demarcation between tumour tissue and healthy tissue.

A further preferred implementation example of the method provides that for every measuring cycle real-time software in a control and read-out module of a multiwire ionization chamber calculates the actual value of the ion beam width from the raw detector data of the multiwire ionization chamber. In that case, a procedure is preferably carried out in which the beam full width at half maximum is varied and set from measuring cycle to measuring cycle, calculation of the beam full width at half maximum being performed by collecting raw detector data of a multiwire ionization chamber. Such real-time software has sufficient time between measuring cycle and measuring cycle and/or between adjacent beam positions to re-calculate the appropriate setting data in an adapted form.

In a further preferred implementation example of the method, information on the beam width is supplied to a module for storing the measurement data and for controlling and reading-out. That module may serve, on the one hand, initially to store the raw detector data and to re-correlate the raw detector data from beam position to beam position or from measuring cycle to measuring cycle.

In a further implementation example of the method, a module for storing, controlling and reading-out the actual values of the ion beam spot size is compared in real time with the information on the desired value of the ion beam spot size from an irradiation plan. Using such a module, the size of the ion beam spot not only can be detected and varied between measuring cycle and measuring cycle and/or between beam position and beam position but also can be varied during and within a beam extraction. For that purpose, in a further implementation example of the method, a correction value for magnet power supply units of the quadrupole doublet of the quadrupole magnets of a high-energy radiation guide directly in front of the raster scanner, which quadrupole magnets determine the size of the ion beam spot, can be determined and set accordingly.

If, in a further implementation example of the method, the procedure is carried out from measuring cycle to measuring cycle, a position-measuring system can perform correction and re-setting from one ion beam position in the irradiation plan to the next ion beam position. That re-setting is initially already specified by setting the frequency of tracking of the ion beam in the form of a parameter of real-time software that determines and executes the correction values for the quadrupole doublet. The attenuation of the ion beam width is also adjustable analogously to the frequency of the adaptation by means of a parameter. Finally, threshold values can be established for the ion beam width in respect of maximum and minimum ion beam width in order to exclude the possibility of maladjustment from the outset.

The method according to the invention and the apparatus according to the invention are accordingly concerned with readjustment of the beam width in real time. For that purpose, the information on the course of the beam width with time, which is available from the position measurement of the raster scanning system, is combined with the ability of the control system to apply to magnet power supply units of magnets that influence the size of the ion beam spot, such as quadrupole magnets, new desired values in rapid succession. A control loop is thereby formed which makes it possible for current correction values for the two magnet power supply units of the quadrupole doublet directly in front of the raster scanning magnets to be calculated from a comparison of desired and actual values of the prevailing dimension of the beam and thus for corrected field settings to be produced which improve the focusing state of an ion beam therapy system. It is thus possible for the control to provide for a constant ion beam spot size and to be maintained more reliably during the scanning process and for defined variations of the size of the ion beam spot to be performed in accordance with the specifications of an irradiation plan that can be made considerably more flexible.

Figure 1:
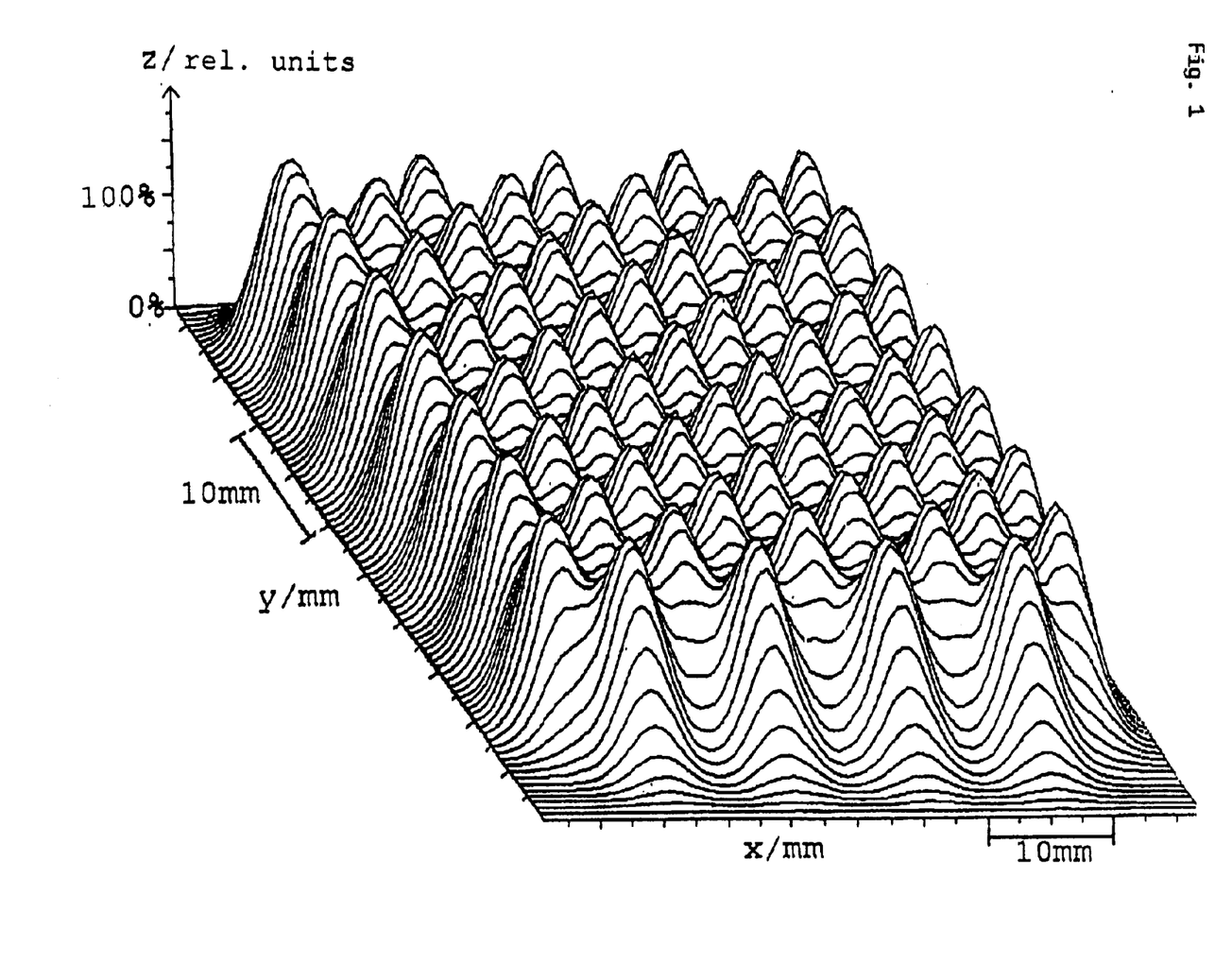
FIG. 1 shows an example of an inhomogeneous dose distribution at too small a beam full width at half maximum.

FIG. 1 shows an example of an inhomogeneous dose distribution at too small a beam full width at half maximum. For that purpose, in FIG. 1 a co-ordinate system is set up in the X, Y and Z directions, the units for the X and Y axes being millimeters and the radiation dose being plotted in the direction of the Z axis. FIG. 1 illustrates the effect on the homogeneity of the dose distribution of a beam profile width not conforming to specifications of a radiation plan. An inhomogeneity that is unacceptable for tumour irradiation is to be seen at the irradiation dose maxima projecting in the Z direction.

In principle, the beam profile width is too narrow in relation to the beam position spacings or, conversely, the beam position spacings are too large for the set beam profile width. An essential objective of beam application is not achieved, therefore, namely the production of a particle allocation that is as exact as possible, that is to say, within the target volume the deviations from the planned dose distribution are to be minimal, and therefore an irradiation inhomogeneity is obtained for the beam profile width set in FIG. 1 and the specifications of the irradiation plan cannot be met.

FIG. 2 shows an example of a homogeneous dose distribution at an adequate beam full width at half maximum. In FIG. 2, once again an X, Y and Z co-ordinate system is shown with a millimeter scale on the X and Y axes and a dose quantity in the direction of the Z axis. In this embodiment, a sensible ratio of beam profile width to beam position spacing is maintained during the irradiation, with the result that a homogeneous dose distribution that satisfies the medical requirements is obtained in the tumour volume and a relatively steep drop towards the edge of the irradiation can be achieved. For that to occur, however, a considerably smaller beam position spacing and, therewith, considerably more beam positions than in FIG. 1 have to be planned in FIG. 2, with the result that the treatment time in FIG. 2 would be many times greater than the treatment time in FIG. 1. By means of the present invention, however, the beam width can be varied from beam position to beam position, so that, as the beam position spacing becomes greater, the beam profile width can be set wider and, towards the edge, the beam position spacing can be reduced while simultaneously reducing the beam profile width.

By means of the apparatus according to the invention, therefore, considerably more homogenised dose distribution can be obtained, as FIG. 2 shows, and, at the same time, the number of beam positions per iso-section through tumour tissue can be reduced and, towards the edge of the tumour, the beam position spacing is reduced and simultaneously the beam profile width is reduced, as FIG. 3 shows, so that a steep edge drop and a more precise demarcation from healthy tissue becomes possible.

FIG. 3 shows an illustrative embodiment of a beam position distribution that becomes possible by employing the apparatus according to the invention. The apparatus according to the invention allows adaptation of the size of an ion beam spot in tumour irradiation with a raster scanning device composed of raster scanning magnets for raster scanning the ion beam, with quadrupole magnets determining the size of the ion beam spot which are arranged directly in front of the raster scanning magnets, with two magnet power supply units of the quadrupole doublet of the quadrupole magnets determining the size of the ion beam spot, the apparatus having a control loop that provides current correction values, by comparing desired and actual values of the prevailing dimension of the beam, for two magnet power supply units of the quadrupole doublet arranged directly in front of the raster scanning magnets and that makes possible a defined homogenization and/or a defined variation of the size of the ion beam spot during beam extraction and/or from measuring cycle to measuring cycle and/or from beam position to beam position.

FIG. 3 shows for that purpose tumour tissue 1 surrounded by healthy tissue 2 and a sharply defined edge 3 which represents the boundary tissue between tumour tissue 1 and healthy tissue 2. Using the above-mentioned apparatus according to the invention, the beam profile width is set wider in the centre 4 of the tumour tissue than in the edge region 9 of the tumour tissue 1. In return, a fine beam position raster is provided in the edge region 9, which is this embodiment has four times the density per unit of area in the edge region 9 compared with the density per unit of area in the centre 4.

Owing to the regulation of the beam width according to the invention, which acts directly on the quadrupole doublet arranged in front of the raster scanning magnets, both in the horizontal and in the vertical direction, it is possible, despite the coarse beam position raster in the centre 4 of the tumour tissue, to obtain a homogenization of the dose distribution and, at the same time, a homogeneous dose distribution also in the edge region 9 with a considerably more precise demarcation of the edge region of the tumour tissue 1 from the healthy tissue 2 by virtue of the adaptation of the size of the ion beam spot from beam position to beam position during the irradiation. That adaptation can be carried out not only from beam position to beam position but also from measuring cycle to measuring cycle and, to stabilise the dose distribution, also during beam extraction. For that purpose, an additional control loop is provided between a control and read-out module and magnet power supply units for horizontal and vertical quadrupoles arranged directly in front of the scanning magnets.

Accordingly, a narrow ion beam spot over a closely spaced beam position raster is implemented for irradiation of the isoenergy section in the edge region and a large beam spot over a coarse beam position raster in the centre. Thereby, the total number of beam positions per isoenergy cross-section and hence the duration of the irradiation can advantageously be markedly reduced, and the dose gradient at the edge can be selected to be very steep when specifying the irradiation plan.

Figure 4:
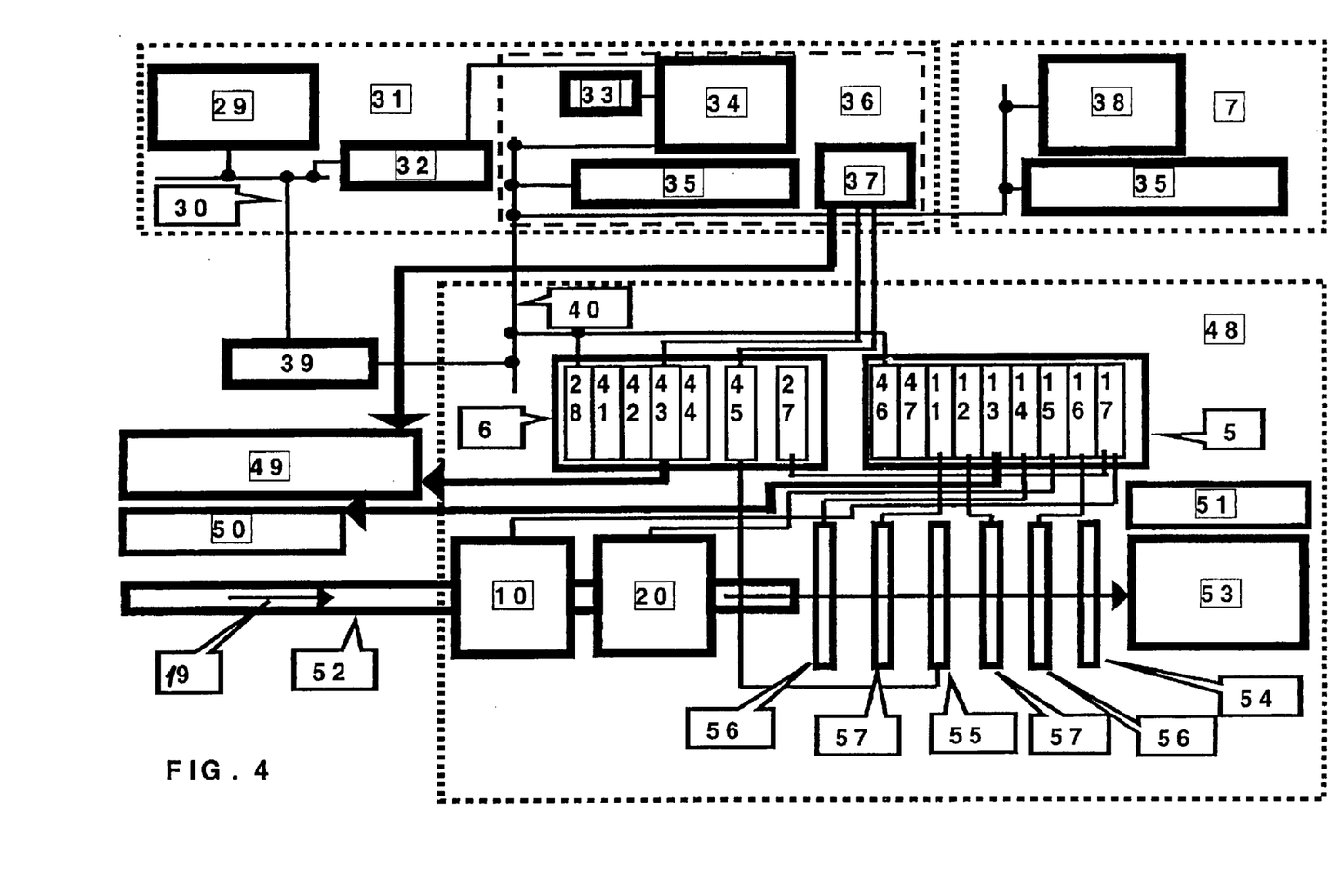
FIG. 4 shows an embodiment of an irradiation system in which the apparatus according to the invention can be employed.

FIG. 4 shows an embodiment of an irradiation system in which the apparatus according to the invention can be employed. The control and monitoring of the irradiation system is ensured in this case by a complex electronic system.

The control and monitoring system is composed of three levels, namely a sequence control 5, a system control 6 and an operator control 7. These operate independently of one another. Distributed over all three levels is a safety system 8 which ensures immediate switching-off of the beam in the event of a fault in the system.

The sequence control 5 allows access by the operator control 7 only during initialisation at the start and in the case of emergency stop. During the irradiation, the sequence control 5 operates automatically. In addition to control functions, it also fulfils safety functions whereby the measured data are compared with the specifications of the irradiation plan and result in the beam being switched off in the event of deviation above fixed limits.

The system control 6 allows setting of the operating parameters, for example of the detector voltage. In addition, the system control 6 monitors processes that take place "slowly" by reading out a large number of system states and switches off the beam where appropriate.

The operator control 7 allows the operator to interact with the control and monitoring system. From the operator control, irradiation plans are loaded into the sequence control 5, irradiations are started, stopped or interrupted, operator actions and system parameters are logged, the irradiation process and the system state are visualised by reference to measurement data and the measured data are archived to produce document scenarios.

The control and monitoring system is implemented in the form of a VME environment and has operating devices such as input/output devices (terminals) and a computer system consisting of several individual computers with the customary peripherals. The devices for monitoring the beam as to position, width and intensity and the device for requesting and deflecting the beam are coupled to the VME environment via bus lines.

The safety system, which operates independently of the sequence control 5, monitors the aggregate radiation process for the entire duration of the irradiation. It interrupts the irradiation process automatically if, owing to a malfunction, the deflection of the beam is faulty or the particle number for a point or a layer or the total number of particles applied is exceeded. The cause of a malfunction may lie in the actual production of the beam or may have its basis in the sequence control 5, the sequence control 5 having, however, auto-monitoring means for interrupting the irradiation process.

The sequence control 5 has circuit modules (control and read-out modules 11–17) which are connected to the operating devices by a common system bus. The system bus is in the form of a VME bus.

Each of the control modules 11 to 17 is connected by a respective separate device bus to a measuring device (such as an ionization chamber, multiwire chamber etc.) and to an external storage device 27. The device buses are independent of the system bus. The block diagram shown by FIG. 4 accordingly belongs to a control system for an ion beam therapy unit.

The control system for an ion beam therapy unit accordingly consists essentially of a technical control room (TKR) in which all of the accelerator data of the Ethernet are assembled on an accelerator operating console and Ethernet router data are passed to the next larger unit of the control system for an ion beam therapy unit of the technical operating console in the therapy itself. The central device of that technical operating console is the therapy operating computer (TORT) which has a barcode reader (BCL) and which is in communication with the operating element of the terminals via the therapy Ethernet. The technical operating console in the therapy domain has a medical operating console (MBDK) which is in communication with a therapy domain (Cave M) and has a direct connection for triggering beam termination of the accelerator. For beam termination, a resonant quadrupole (S02Q1E) for the slow extraction of the beam is zeroed via its power supply unit via an interlock unit in the bus system of the therapy control system. A deflecting dipole magnet (TH3MU1) of the beam guide to the therapy measuring position is likewise zeroed by the interlock unit (ILE) in the bus system (VME) of the therapy control system in order to terminate the beam or the extraction in the event of a fault.

For the system control (VMESK) per se several microprocessors work together on a bus system connection frame (VME crate). In addition to the data store (ODS) for online display mentioned above and shown in FIG. 4, the system control includes an intensity monitor (IMON) which co-operates inter alia with an ionization chamber and the read-out electronics for monitoring the total particle number. In addition, a Trottmann circuit unit (TME) for monitoring the operating ability of the processors is present in the system control. In addition to the interlock unit (ILE) already mentioned and a control bus adapter (KBA), the system control has an analogue/digital module (ADIO) and a system control computer (SKR) in the bus system (VME) of the system control.

Figure 5:
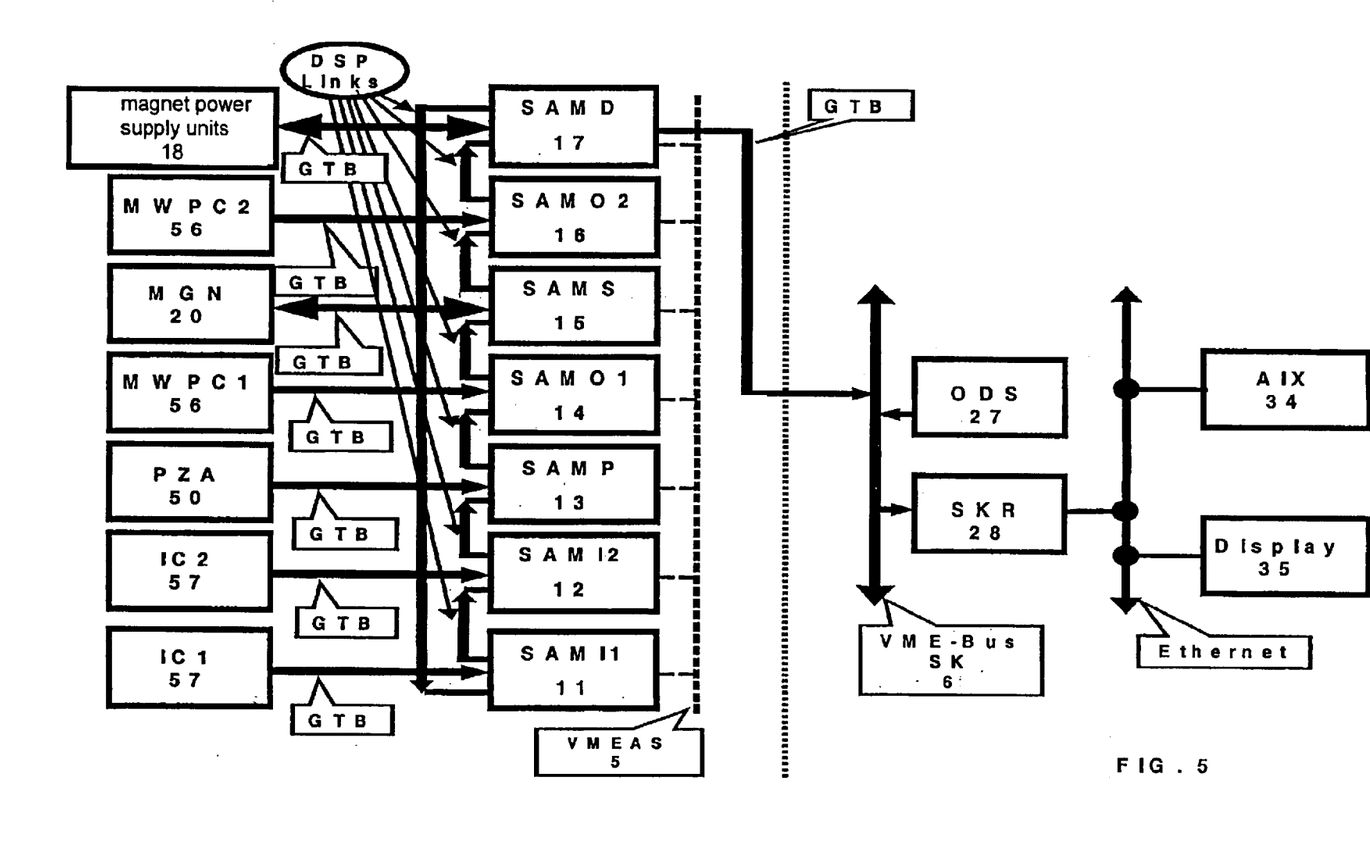
FIG. 5 shows a data flow diagram of an illustrative embodiment of the invention.

The components of the sequence control (VMEAS) are identical to the components of the data flow diagram shown in FIG. 5, the not shown, that exclusively fulfils the function of width regulation. The capacity of the arrangement shown is entirely adequate, however, for undertaking the additional task of a width regulation of the ion beam in co-operation with the magnet power supply units 18 and a control loop between the SAMD, the SAMO1 magnet power supply units 18 of the horizontal and vertical quadrupole magnets 10.

LIST OF REFERENCE NUMERALS 1 tumour tissue
2 healthy tissue
3 edge of tumour tissue
4 centre of tumour tissue
5 sequence control system
6 system control
7 operator control
8 safety system
9 edge region
10 quadrupole magnets for horizontal and vertical focusing
11 control and read-out module SAMI1
12 control and read-out module SAMI2
13 control and read-out module SAMP
14 control and read-out module SAMO1
15 control and read-out module SAMS
16 control and read-out module SAMO2
17 control and read-out module SAMD
18 magnet power supply units for horizontal and vertical quadrupoles
19 ion beam
20 raster scanning magnets
27 ODS (data store)
28 SKR (system control computer)
29 accelerator operating console in TKR
30 accelerator Ethernet
31 technical control room, therapy, TKR
32 Ethernet router
33 barcode reader, BCL
34 therapy operating computer, TORT
35 operating elements, terminals
36 technical operating console, therapy
37 medical operater console, therapy
38 therapy operating computer, TORM
39 Ethernet bridge
40 therapy Ethernet
41 analogue/digital IO module, ADIO
42 control bus adapter, KBA
43 interlock unit, ILE
44 Totmann unit, TME
45 intensity monitor, IMON
46 sequence control computer, ASR
47 digital IO module, DIO
48 therapy Cave M
49 separate magnet power supply unit control for terminating beam of accelerator (S02KQ1E and TH3MU1)
50 to pulse centre of accelerator, PZA
51 PET camera
52 accelerator beam guide into Cave M
53 patient couch
54 mini-ridge filter
55 ionization chamber for intensity monitor
56 multiwire chamber (multiwire proportional chamber, MWPC)
57 ionization chamber for intensity measurement (IC)

What is claimed is:

1. Apparatus for adapting the size of an ion beam spot, having the following features:

a raster scanning device composed of raster scanning magnets (20) for raster scanning the ion beam (19), quadrupole magnets (10) determining the size of the ion beam spot, which quadrupole magnets (10) are arranged directly in front of the raster scanning magnets (20), two magnet power supply units (18) for the quadrupole doublet of the quadrupole magnets (10) determining the size of the ion beam spot, and a control loop for providing current correction values, by comparing desired and actual values of the prevailing dimension of the beam, for two magnet power supply units (18) of the quadrupole doublet of the quadrupole magnets (10) determining the size of the ion beam spot, for defined homogenization and/or for defined variation of the size of the ion beam spot during beam extraction and/or from measuring cycle to measuring cycle and/or from beam position to beam position, the apparatus having a control and read-out module (SAMD) that controls and reads out a denser ion beam position raster with, at the same time, a smaller ion beam spot size in the edge region (3) than in the volume region (4) of a tumour.

2. Apparatus according to claim 1, wherein the apparatus has a position-sensitive detector (MWPC1) for detecting the ion beam width and for producing raw detector data.

3. Apparatus according to claim 1, wherein the apparatus has a plurality of control and read-out modules (SAMO1 and SAMD) and associated data connections in order to send information on the actual value of ion beam widths to a storage, control and read-out module (SAMD) for storage of the measurement data.

4. Apparatus according to claim 1, wherein one read-out module (SAMD) had a number of free interfaces and a computing capacity by means of which the tracking of the ion beam width can be performed.

5. Apparatus according to claim 1, wherein the apparatus has a control system that is expanded by one control and read-out module, wherein exclusively the function of ion beam width regulation can be performed by the additional control and read-out module.

6. Apparatus according to claim 1, wherein the apparatus has a control loop which starts from a multiwire ionization chamber (MWPC1) with attached control and read-out module (SAMO1) and leads to a control and read-out module (SAMD) that provides measurement data for graphical representation and actuates two magnet power supply units (18) for horizontal and vertical focusing of the quadrupole doublet directly in front of the raster scanning magnets (20).

7. Method for adapting the size of an ion beam spot in tumour treatment, wherein the method steps:

dynamic adaptation of the size of the beam spot in real time by, applying desired values for different ion beam sizes to the quadrupole magnet (10) determining the beam size between two successive accelerator cycles or within an acceleration cycle by means of adjustable frequency, obtaining current correction values, by comparing desired and actual values of the prevailing dimension of the beam, for two magnet power supply units (18) of the quadrupole doublet of the quadrupole magnets (10) determining the size of the ion beam spot, for defined homogenization and/or for defined variation of the size of the ion beam spot during beam extraction and/or from measuring cycle to measuring cycle and/or from beam position to beam position, irradiating tumour tissue (1) with a denser ion beam position raster and, at the same time, a smaller ion beam spot size in the edge region (3) than in the volume region (4) of the tumour.

8. Method according to claim 7, wherein the beam full width at half maximum is adapted to the ion beam position raster in such a way that, in the case of the fine ion beam position raster in the edge region (3), a smaller beam full width at half maximum is set than in the volume region (4) of the tumour with a coarse ion beam position pattern.

9. Method according to claim 7, wherein for every measuring cycle real-time software in a control and read-out module (SAMO1) of a multiwire ionization chamber (MWPC1) calculates the actual value of the ion beam width from the raw detector data of the multiwire ionization chamber (MWPC1).

10. Method according to claim 7, wherein information on the beam width is supplied to the module (SAMD) for storing the measurement data and for controlling and reading-out.

11. Method according to claim 10, wherein, in the module (SAMD) for storing, controlling and reading-out, the actual value of the ion beam spot size is compared in real time with the information on the desired value of the ion beam spot size from an irradiation plan.

12. Method according to claim 7, wherein a correction value for magnet power supply units (18) of the quadrupole doublet of the quadrupole magnets (10) of a high-energy beam guide directly in front of the raster scanner, which quadrupole magnets (10) determine the size of the ion beam spot, is determined and set.

13. Method according to claim 7, wherein a correction or resetting is performed from measuring cycle to measuring cycle of a position-measuring system or from one ion beam position in the irradiation plan to the next ion beam position.

14. Method according to claim 7, wherein setting of the frequency for tracking the ion beam width in the form of a parameter of real-time software that determines the correction values for the quadrupole doublet is carried out.

15. Method according to claim 14, wherein tracking of the ion beam width is adjustably attenuated.

16. Method according to claim 15, wherein threshold values for the ion beam width are established.

17. Method according to claim 14, wherein threshold values for the ion beam width are established.

* * * * *